United States Patent [19]

Bonutti

[11] Patent Number: 5,464,426
[45] Date of Patent: Nov. 7, 1995

[54] METHOD OF CLOSING DISCONTINUITY IN TISSUE

[76] Inventor: Peter M. Bonutti, 1303 W. Evergreen Plz., Effingham, Ill. 62401

[21] Appl. No.: 207,297

[22] Filed: Mar. 7, 1994

Related U.S. Application Data

[63] Continuation-in-part of Ser. No. 62,295, May 14, 1993, Pat. No. 5,403,348.

[51] Int. Cl.⁶ .................................................. A61B 17/04
[52] U.S. Cl. ........................................... 606/232; 606/216
[58] Field of Search ................................ 606/215, 216, 606/232; 128/898

[56] References Cited

U.S. PATENT DOCUMENTS

| | | | |
|---|---|---|---|
| 2,199,025 | 4/1940 | Conn | 606/232 |
| 3,625,220 | 12/1971 | Harvey | 606/232 |
| 3,648,705 | 3/1972 | Lary | 606/232 |
| 4,210,148 | 7/1980 | Stivala | 606/232 |
| 4,235,238 | 11/1980 | Ogiu et al. | |
| 4,409,974 | 10/1983 | Freedland | |
| 4,448,194 | 5/1984 | DiGiovanni et al. | 606/144 |
| 4,669,473 | 6/1987 | Richards et al. | |
| 4,741,330 | 5/1988 | Hayhurst | |
| 4,750,492 | 6/1988 | Jacobs | |
| 4,823,794 | 4/1989 | Pierce | 606/232 |
| 4,898,156 | 2/1990 | Gatturna et al. | |
| 4,968,315 | 11/1990 | Gatturna | |
| 5,009,663 | 4/1991 | Broomé | 606/232 |
| 5,037,422 | 8/1991 | Hayhurst et al. | |
| 5,041,129 | 8/1991 | Hayhurst et al. | |
| 5,046,513 | 9/1991 | Gatturna et al. | 128/892 |
| 5,053,047 | 10/1991 | Yoon | 606/232 |
| 5,100,417 | 3/1992 | Cerier et al. | |
| 5,102,421 | 4/1992 | Anspach, Jr. | 606/232 |
| 5,123,914 | 6/1992 | Cope | 606/232 |
| 5,141,520 | 8/1992 | Goble et al. | 606/232 |
| 5,156,616 | 10/1992 | Meadows et al. | 606/232 |
| 5,176,682 | 1/1993 | Chow | 606/72 |

*Primary Examiner*—Gary Jackson
*Attorney, Agent, or Firm*—Tarolli, Sundheim & Covell

[57] ABSTRACT

When a discontinuity in body tissue is to be closed, a suture is inserted through openings in a plurality of anchors. A thin elongated member, such as a needle or K-wire, is also inserted through the openings in the anchors. The thin elongated member is then inserted through the body tissue at a first location along one side of the discontinuity in the body tissue. A first anchor is then pushed through the body tissue from the inner side of the body tissue to the outer side of the body tissue with the suture extending through the opening in the anchor. The thin elongated member is then withdrawn from the body tissue and subsequently inserted through the body tissue at a second location disposed along the second or opposite side of the discontinuity. The next succeeding anchor in the array of anchors on the suture and thin elongated member is then pushed through the body tissue at the second location. Pulling on the suture presses the anchors against the body tissue and presses the body tissue together. The anchors may be pushed through the body tissue with a pusher member or by pushing the anchors against each other.

71 Claims, 4 Drawing Sheets

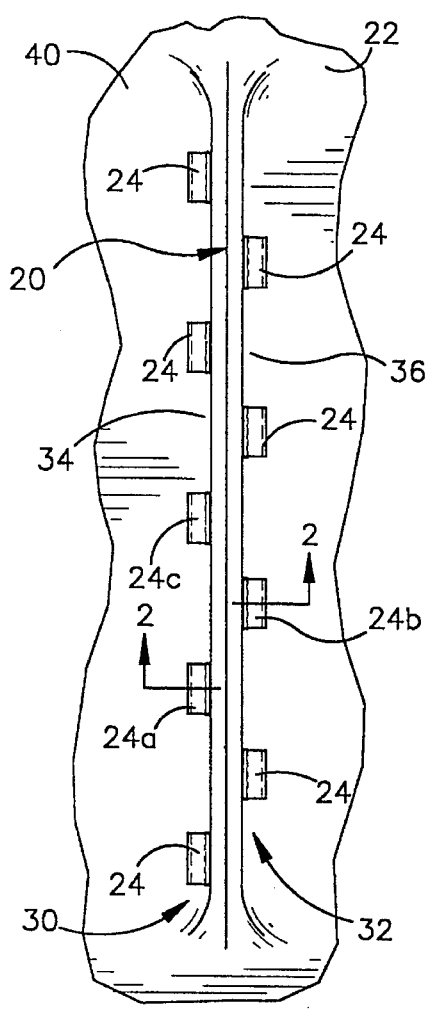
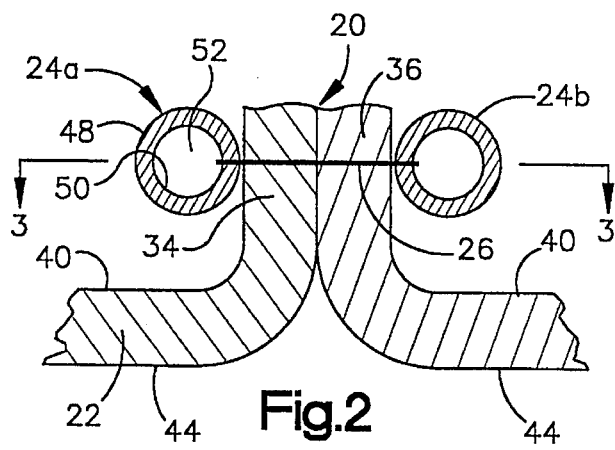
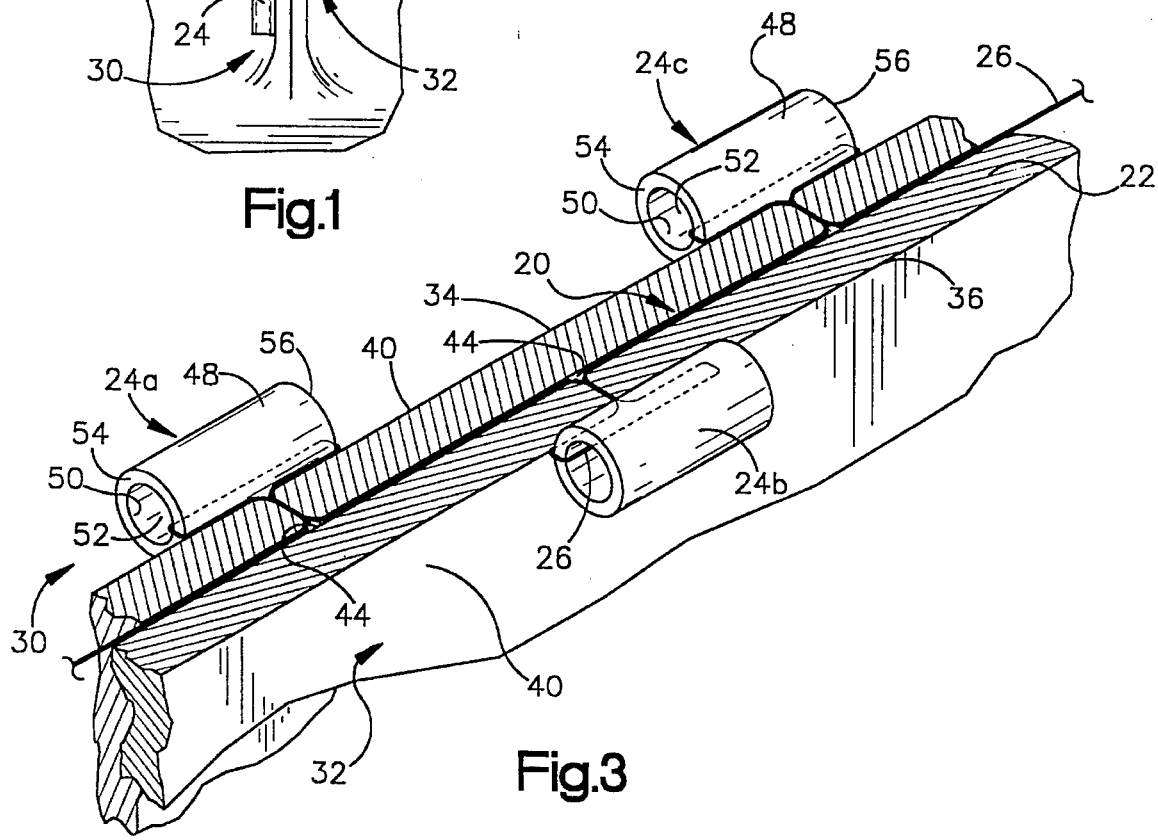

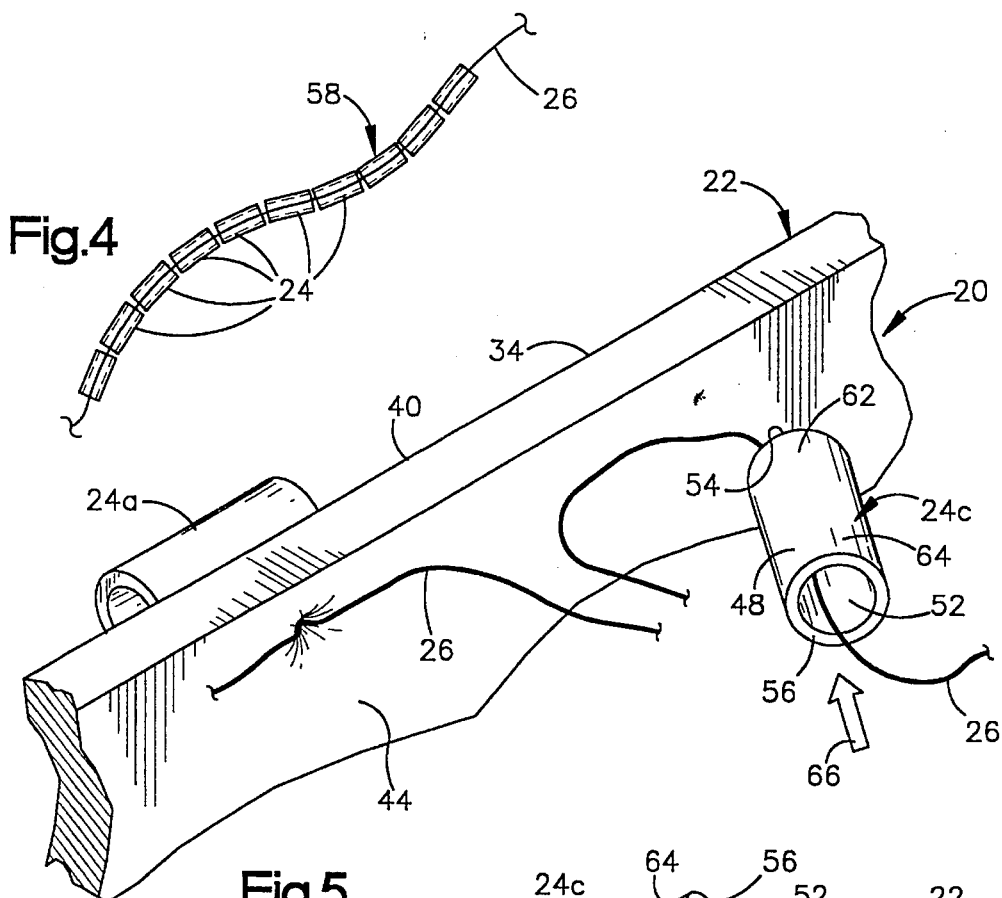
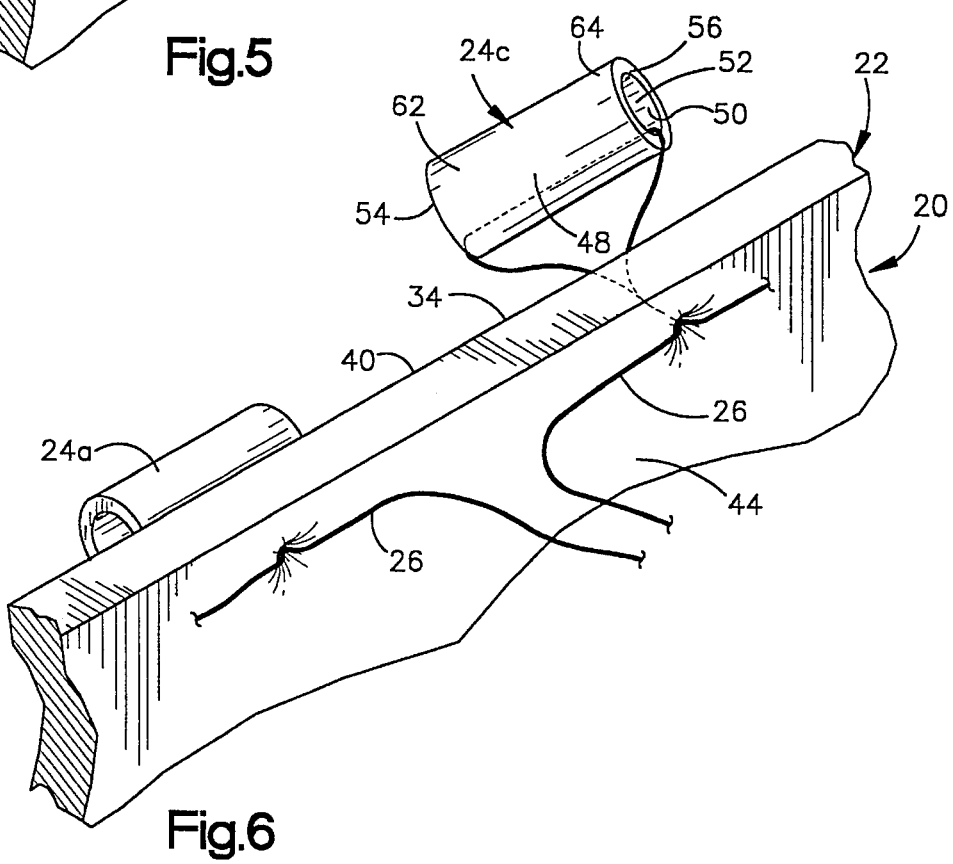

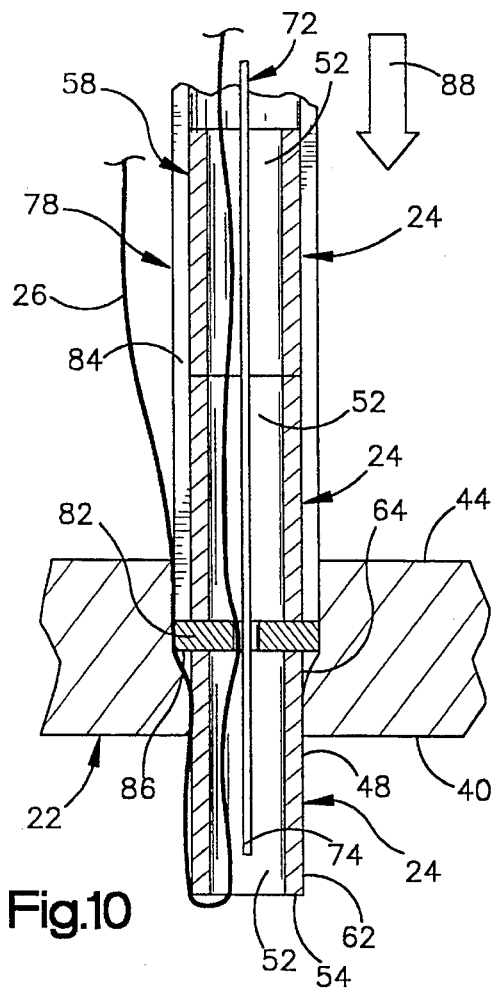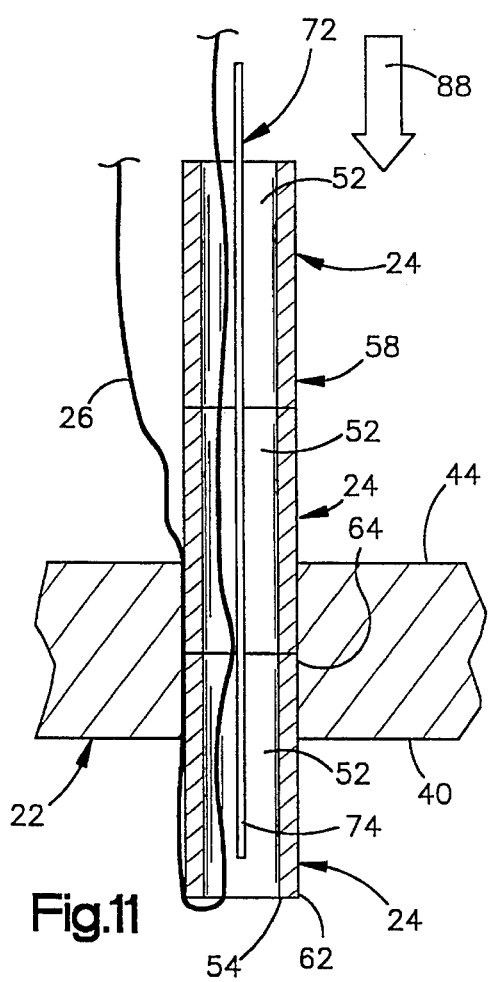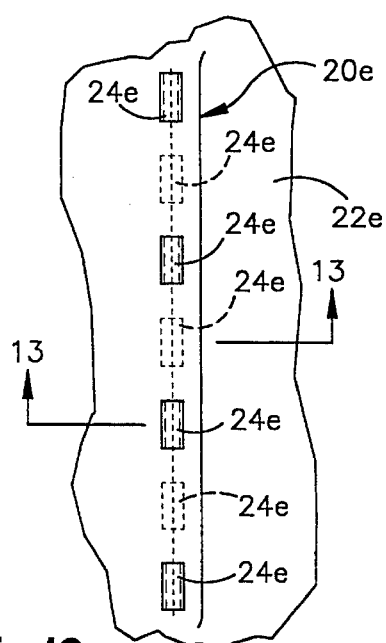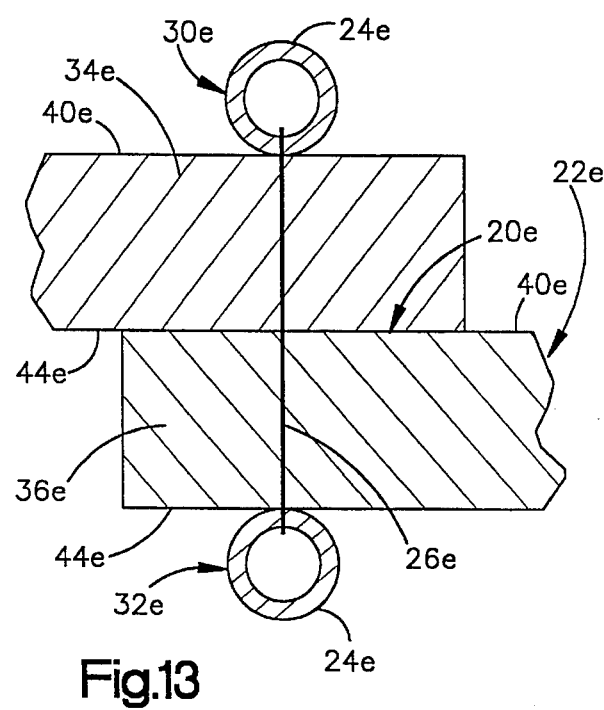

5,464,426

METHOD OF CLOSING DISCONTINUITY IN TISSUE

RELATED APPLICATION

This application is a continuation-in-part of U.S. patent application Ser. No. 08/062,295 filed May 14, 1993, now U.S. Pat. No. 5,403,348, by Peter M. Bonutti and entitled "Suture Anchor". The benefit, under Title 35, United States Code, paragraph 120, of the aforementioned application is hereby claimed.

BACKGROUND OF THE INVENTION

The present invention relates to a new and improved method of closing a discontinuity in body tissue.

A method and apparatus for closing a discontinuity in body tissue is disclosed in U.S. Pat. No. 4,448,194 issued May 15, 1984. This patent discloses the use of a fastener to close a discontinuity, such as a wound or incision, in body tissue. The fastener includes a filament which extends between rod-shaped heads of the fastener.

Another method of closing a discontinuity in body tissue is disclosed in U.S. Pat. No. 4,823,794 issued Apr. 25, 1989. This patent discloses the use of a pair of pledgets in combination with a suture. The pledgets are disposed along opposite sides of the discontinuity in the body tissue and are interconnected by a suture. The suture is drawn tight to close the space between opposite sides of the discontinuity and is then tied to hold the pledgets in place.

SUMMARY OF THE INVENTION

The present invention provides a new and improved method of closing a discontinuity in body tissue. When a discontinuity in body tissue is to be closed, a suture is inserted through openings in anchors to provide a series of anchors on the suture. In addition, a thin elongated member may be inserted through the openings in the anchors.

The thin elongated member is then inserted through body tissue at a first location disposed along a first side of the discontinuity. A first anchor is then pushed through the body tissue with the suture extending through the opening in the first anchor. The thin elongated member is then inserted through body tissue at a second location disposed along a second side of the discontinuity. A second anchor is pushed through the body tissue with the suture extending through the opening in the second anchor.

BRIEF DESCRIPTION OF THE DRAWINGS

The foregoing and other features of the invention will become more apparent upon a consideration of the following description taken in connection with the accompanying drawings, wherein:

FIG. 1 is a schematicized plan view of a body tissue discontinuity which has been closed with a suture and a plurality of anchors;

FIG. 2 is a sectional view, taken generally along the line 2—2 of FIG. 1, illustrating the relationship between anchors disposed along opposite sides of the discontinuity and a suture which extends through openings in the anchors;

FIG. 3 is a schematicized sectional view, taken generally along the line 3—3 of FIG. 2, further illustrating the relationship of the anchors and suture to the discontinuity in the body tissue;

FIG. 4 is an illustration depicting the manner in which an array or series of anchors is positioned on a suture in preparation to undertake the closing of a discontinuity in body tissue;

FIG. 5 is a schematicized illustration depicting the manner in which an anchor is oriented relative to an inner side of the body tissue prior to being pushed through the body tissue;

FIG. 6 is a schematic illustration depicting the manner in which an anchor is positioned relative to the body tissue by pulling on a suture after the anchor has been pushed through the body tissue;

FIG. 10 is a schematic sectional view depicting the manner in which a pusher member is used to push an anchor along the thin elongated member and through the body tissue;

FIG. 11 is a schematic sectional view, generally similar to FIG. 10, illustrating a third method in which force is transmitted between anchors to move an anchor through the body tissue;

FIG. 12 is a schematic plan view, generally similar to FIG. 1, of an alternative manner of closing a discontinuity in body tissue; and FIG. 13 is a schematic sectional view, taken along the line 13—13 of FIG. 12, further illustrating the alternative manner of closing the discontinuity.

DESCRIPTION OF SPECIFIC PREFERRED EMBODIMENTS OF THE INVENTION

Closure

Figure 7:
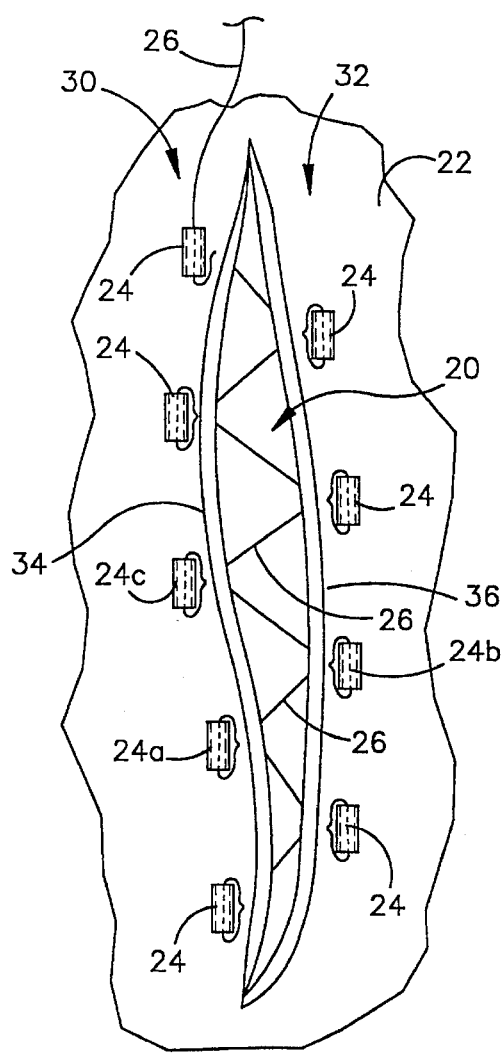
FIG. 7 is a schematic illustration depicting the manner in which a discontinuity in body tissue is loosely closed prior to pulling on a suture.

A discontinuity 20 (FIG. 1) in body tissue 22 is closed by a plurality of anchors 24 which are interconnected by a suture 26 (FIG. 2). The discontinuity 20 may be a wound or incision in the body tissue 22. The anchors 24 are disposed in arrays 30 and 32 (FIG. 1) along opposite sides of the discontinuity 20. Thus, the array 30 of anchors 24 is disposed along the left side 34 of the body tissue discontinuity 20 and the array 32 of anchors is disposed along the right side 36 of the discontinuity. The discontinuity 20 may be an incision, wound or other opening in the body tissue 22.

The suture 26 extends back and forth across the discontinuity 20 between the left and right arrays 30 and 32 of anchors 24. Thus, the suture 26 extends through an opening in an anchor 24a (FIG. 1) on the left side of the discontinuity 20. The suture 26 extends from the anchor 24a across the discontinuity 20 to an anchor 24b on the right side of the discontinuity. The suture 26 extends through an opening in the anchor 24b on the right side of the discontinuity 20. The suture 26 extends from the anchor 24b across the discontinuity 20 to an anchor 24c on the left side 34 of the discontinuity.

Thus, a single suture 26 extends back and forth across the discontinuity 20 between each of the anchors 24 in the left and right arrays 30 and 32 of anchors. Each of the anchors 24 along the left side 34 of the discontinuity 20 is offset longitudinally along the discontinuity from adjacent anchors along the right side 36 of the discontinuity.

Tension in the suture 26 presses the anchors 24 against the opposite sides 34 and 36 of the discontinuity 20 (FIG. 3). Thus, the suture 26 applies force against the anchor 24a to press the anchor against an outer side surface 40 of the body tissue 22 on the left side 34 of the discontinuity 20. Similarly, the suture 26 presses the anchor 24b against the outer side surface 40 of the body tissue 22 on the right side 36 of the discontinuity 34.

The force applied against the outer side surface 40 of the body tissue 22 by the anchors 24 presses an inner side surface 44 (FIGS. 2 and 3) on the body tissue 22 on the left side 34 of the discontinuity 20 against the inner side surface of the body tissue on the right side 36 of the discontinuity (FIG. 3). The suture 26 extends between the inner side surface 44 on the left and right sides 34 and 36 of the discontinuity 20. Tension in the suture 26 pulls the anchors 24a and 24c toward the right (as viewed in FIG. 3) and pulls the anchor 24b toward the left. This results in surface areas on the inner side surface 44 of the body tissue 22 on opposite sides of the discontinuity 20 being pressed together.

The anchors 24 (FIGS. 2 and 3) all have the same hollow cylindrical configuration. Thus, the anchor 24a has a cylindrical outer side surface 48 which is pressed against the outer side surface 40 of the body tissue 20 by the suture 26. The anchor 24a has a cylindrical inner side surface 50 which defines a cylindrical opening or passage 52 through which the suture 26 extends. The anchor 24a has a pair of parallel end surfaces 54 and 56 across which the suture 26 extends. The anchor 24a has the same construction as is disclosed in U.S. patent application Ser. No. 08/062,295 filed May 14, 1993 by Peter M. Bonutti and entitled "Suture Anchor". Of course, the anchors 24 could have a different construction if desired.

The discontinuity 20 (FIG. 1) is closed by using a single suture and nine identical anchors 24. However, it is contemplated that the number of anchors which are used to close a discontinuity in body tissue 22 will depend on the length of the discontinuity. Thus, any desired number of anchors may be used. For example, only two anchors 24 may be required to close a relatively small discontinuity 20 while more than nine anchors may be required to close a relatively large discontinuity.

Although it is preferred to use anchors 24 having a hollow cylindrical construction, anchors having a different construction could be used if desired. Regardless of the construction of the anchor 24, a suture 26 would extend through an opening in each of the anchors and urge them toward each other to press the body tissue along the left and right sides 34 and 36 of the discontinuity together.

The suture 26 may be a thread, wire or other biocompatible material. The suture 26 may be formed of a material which is absorbable or nonabsorbable by the body tissue 22. The body tissue 22 may be any desired portion of the human body. The body tissue 22 may be internal or external body tissue. Thus, the body tissue 22 may be a portion of the skin, ligament, bone, muscle, cartilage or other component of a human body.

Method of Closure

When a discontinuity 20 in body tissue 22 is to be closed, a suture 26 is inserted through the openings or passages 52 in a plurality of anchors 24 (FIG. 4). This results in an array or series 58 of anchors 24 being disposed on the suture 26.

The number of anchors 24 which are strung onto the suture 26 advantageously exceeds the number of anchors which it is anticipated may be required to close the discontinuity 20. Of course, if an insufficient number of anchors 24 is strung on the suture 26 and additional anchors are required, the suture can be inserted through the additional anchors when the discontinuity 20 is partially closed.

Once the suture 26 has been inserted through the anchors 24, the anchors are pushed through the body tissue 22 at locations which are offset along opposite sides of the discontinuity 20 (FIGS. 3 and 5). Thus, one of the anchors 24 on the suture 26 is pushed through the body tissue 22 along the left side 34 of the discontinuity 20 (FIG. 5). The next succeeding anchor 24 on the suture 26 is pressed through the body tissue along the right side 36 of the discontinuity 20 at a location which is offset along the discontinuity from the first anchor. Each of the anchors 24 on the suture 26 (FIG. 4) is pushed through the body tissue along one of the sides 34 or 36 (FIG. 1) of the discontinuity 20 so that successive anchors are at offset locations along opposite sides of the discontinuity.

The suture 26 extends through the anchors 24 as they are pushed through the body tissue 22. Thus, the suture 26 extends through the cylindrical opening 52 and across an annular leading end surface 54 (FIGS. 3 and 5) of an anchor 24 as it is pushed through the body tissue 22. The suture 26 is pulled or tensioned to move the inner side surface 44 on opposite sides 34 and 36 of the discontinuity into abutting engagement in the manner illustrated in FIG. 3. As this occurs, a portion of the suture 26 is pulled from within an opening 52 in an anchor 24.

When an anchor, for example, the anchor 24c (FIG. 5), is to be positioned along the left side 34 of the discontinuity 20, the anchor 24c is positioned in alignment with the location where it is to be pushed through the body tissue. Thus, a leading end portion 62 of the anchor 24c is positioned in engagement with the inner side surface 44 of the body tissue. At this time, the cylindrical outer side surface 48 of the anchor 24c extends perpendicular to the inner side surface 44 of the body tissue 22 along the left side 34 of the discontinuity 20. The suture 26 extends through the anchor 24c and across the annular leading end surface 54 of the anchor.

Force is applied to the anchor 24c to push the leading end portion 62 of the anchor through the inner side surface 44 of the body tissue 22. Continued movement of the leading end portion 62 of the anchor 24c through the body tissue 22 results in the leading end portion moving through the outer side surface 40 of the body tissue. Thus, once the anchor 24c has been aligned with a location where it is to be pushed through the body tissue 22 along the left side 34 of the discontinuity 20, force is applied against the trailing end portion 64 of the anchor 24, in the manner indicated by an arrow 66 in FIG. 5. The force applied against the trailing end portion 64 of the anchor 24c is effective to push the anchor through the body tissue 22.

After the anchor 24c has been pushed through the body tissue (FIG. 6), the suture 26 is pulled. As the suture 26 is tensioned, torque is applied to the leading end portion 62 of the anchor 24c to rotate the anchor from the orientation shown in FIG. 5 through the orientation shown in FIG. 6 to the position shown in FIG. 3. Although only the anchors 24a and 24c are illustrated in FIG. 6, it should be understood that the anchor 24b is disposed adjacent to the right side 36 of the discontinuity 20 in the manner illustrated in FIG. 3.

The discontinuity 20 has been shown schematically in

FIG. 7 with the left and right sides of the discontinuity separated to illustrate the manner in which the suture 26 extends between the anchors 24 on the left and right sides 34 and 36 of the discontinuity. However, it should be understood that FIG. 7 is a schematic illustration. It is contemplated that it will probably be desired to pull the suture 26 as each anchor 24 in turn is positioned along a side 34 or 36 of the discontinuity.

Therefore, as each anchor in turn is positioned along a side of the discontinuity 20, the suture 26 is pulled to press the inner side surface 44 (FIG. 3) along the left side 34 of the discontinuity 20 against the inner side surface 44 along the right side 36 of the discontinuity 20. As the suture is pulled and each anchor 24 is positioned in turn along a side 34 or 36 of the discontinuity 20, the suture 26 moves in the opening or passage 52 in the anchor.

Method of Guiding Anchor

It is contemplated that a thin elongated member 72 (FIG. 8) may advantageously be used to guide movement of each of the anchors 24 in turn as the anchor is pushed through the body tissue 22. The thin elongated member 72 may be either a needle or a K-wire. Although the thin elongated member 72 has been shown in FIG. 8 as having a linear configuration, it is contemplated that the thin elongated member 72 could have a curving configuration if desired.

When the thin elongated member 72 is to be used to assist in guiding movement of anchors 24 through the body tissue 22, the thin elongated member is inserted through the central openings or passages 52 through each of the anchors 24. Although it is preferred to first insert the suture 26 through the openings 52 in the anchors 24 (FIG. 4) and then to insert the thin elongated member 72 through the openings in the anchors, the thin elongated member could be inserted through the openings in the anchors before the suture 26 is inserted through the openings in the anchors. Once the thin elongated member 72 has been inserted through the openings 52 in the anchors 24 (FIG. 8), the anchors are disposed in a linear array and are supported by the thin elongated member.

Figure 8:
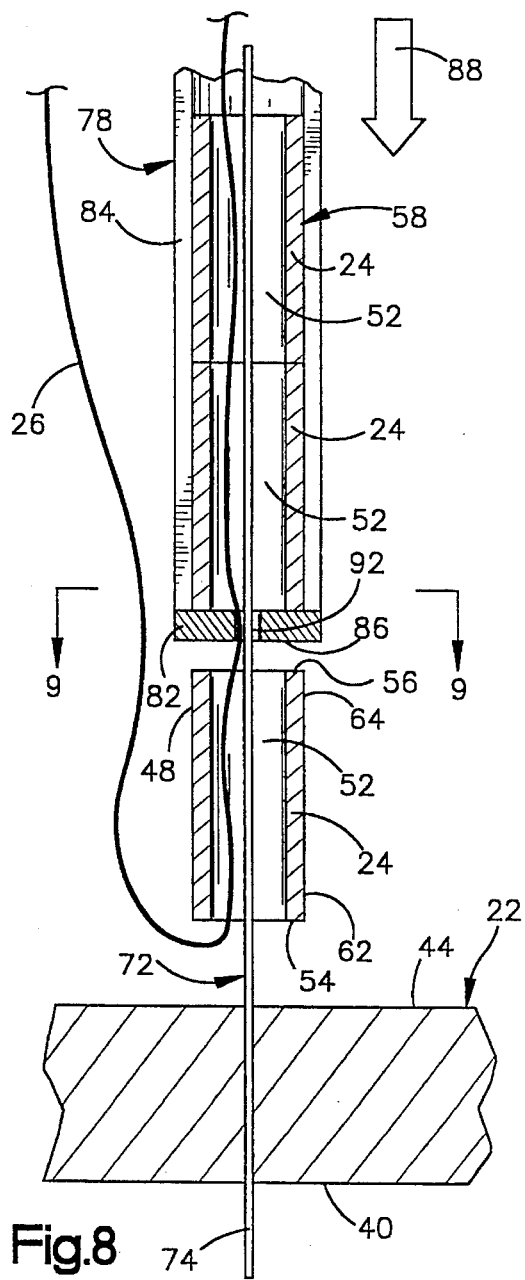
FIG. 8 is a schematic sectional view depicting a method which is similar to the method of FIGS. 1–7 and in which a thin elongated member is used to guide movement of the anchors.

The thin elongated member 72 is then inserted through the body tissue 22 with the anchors 24 disposed in a linear array on the thin elongated member (FIG. 8). A leading end portion 74 of the thin elongated member 72 is inserted through the body tissue from the inner side 44 to the outer side 40. A longitudinal central axis of the thin elongated member 72 extends perpendicular to both the inner and outer side surfaces 44 and 40 of the body tissue 22. Of course, the thin elongated member 72 may be skewed from a perpendicular with the inner and outer side surfaces 44 and 40 if desired.

A leading one of the anchors 24 in the array of anchors on the thin elongated member 72 is then pushed through the body tissue 22 from the inner side 44 to the outer side 40 (FIG. 10). As this occurs, the thin elongated member 72 maintains the cylindrical outer side surface 48 of the anchor 24 in a generally perpendicular relationship with the inner side surface 44 and outer side surface 40 of the body tissue 22. Therefore, the leading end portion 62 of the anchor 24 passes through the inner side surface 44 and then the outer side surface 40 of the body tissue 22 ahead of the trailing end portion 64 of the anchor 24. As this occurs, the suture 26 extends across the leading end surface 54 and along the cylindrical side surface 48 of the anchor 24.

Once the anchor 24 has passed through the body tissue 22 (FIG. 6), the thin elongated member 72 is withdrawn from the body tissue with the remaining anchors in the array 58 of anchors on the thin elongated member and suture 26. The suture 26 is then tensioned. Tensioning the suture 26 applies a force to the leading end portion 62 of the anchor 24 to rotate the anchor in a generally counterclockwise direction (as viewed in FIG. 6). This results in the outer side surface 48 of the anchor 24 being pressed firmly against the outer side surface 40 of the body tissue 22 in the manner illustrated in FIG. 3.

Once the first anchor 24 in an array 58 of anchors on the thin elongated member 72 has been moved through and positioned relative to the body tissue 22 along one side of the discontinuity 20, the thin elongated member is inserted through the opposite side of the discontinuity. The next succeeding anchor, with the suture 26 extending through the central opening 52, is then moved along the thin elongated member 72 and through the body tissue 22 on the opposite side of the discontinuity 20. These steps are repeated until anchors 24 have been positioned along opposite sides 34 and 36 of the discontinuity 20 (FIG. 1) to close the discontinuity.

For example, if the first anchor 24 in a series 58 of anchors on the thin elongated member 72 (FIG. 8) and the suture 26 is to be inserted through the body tissue along the left side 34 of the discontinuity 20, the end portion 74 of the thin elongated member 72 is inserted through the body tissue from the inner side 44 to the outer side 40 (FIG. 8). The first anchor 24 in the series of anchors on the thin elongated member is then moved through the body tissue 22. The thin elongated member 72 is then withdrawn from the body tissue 22 along the left side 34 of the discontinuity 20.

The thin elongated member 72 is then inserted through the body tissue 22 from the inner side 44 along the opposite side, that is the right side 36, of the discontinuity 20. The next anchor 24 is inserted through the inner side surface 44 of the body tissue along the right side 36 of the discontinuity 20. Since the thin elongated member 72 and the anchors 24 are inserted from the inner side 44 of the body tissue, the inner side of the body tissue along opposite sides 34 and 36 of the discontinuity 20 are pressed into abutting engagement with each other by a force transmitted between the anchors 24 by the suture 26 in the manner illustrated in FIG. 2.

Pusher Member

A pusher member 78 (FIGS. 8, 9 and 10) may be used to push each of the anchors 24 in turn through the body tissue 22. The pusher member 78 includes a presser section 82 which is connected to one end of a semi-circular magazine section 84. The presser section 82 has a circular end surface 86 (FIG. 8) which applies force against the trailing end portion 62 of an anchor 24 to press the anchor through the body tissue 22 in the manner illustrated in FIG. 10.

The pusher member 78 is moved toward the inner side surface 44 of the body tissue 22, in the manner indicated by the arrow 88 in FIG. 8. As the lower (as viewed in FIGS. 8 and 10) side 86 of the presser section 82 pushes the leading anchor 24 through the body tissue 22 (FIG. 10), the succeeding anchors in the array 58 of anchors on the thin elongated member 72 are supported in a linear array in the magazine section 84 of the pusher member 78. The suture 26 extends through the cylindrical openings 52 in the anchors 24 and along the outer side surface 48 of an anchor being pushed through the body tissue 22 and the outer side of the pusher member 78 (FIG. 10).

After the leading anchor 24 has been pushed through the body tissue 22, the pusher member 78 and thin elongated member 72 are withdrawn together from the body tissue 22, that is, moved upwardly as viewed in FIG. 10. This results in the leading anchor 24 remaining adjacent to the outer side surface 40 of the body tissue 22. The succeeding anchors 24 remain in the array 58 in the magazine 84.

The thin elongated member is then flexed or resiliently deflected to move the next succeeding or lower (as viewed in FIG. 8) anchor outward from the magazine section 84. Thus, the thin elongated member 72 is moved radially outward of a slot 92 (FIG. 9) in the presser section 82. As this occurs, the next succeeding anchor 24 moves off of the presser section 82 and moves downward (as viewed in FIG. 8) along the suture 26 to position the next succeeding anchor for insertion through the body tissue 22. The remaining anchors 24 in the array of anchors in the magazine section 84 are then supported by the presser section 82.

Figure 9:
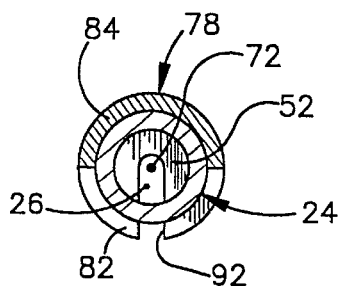
FIG. 9 is a sectional view, taken generally along the line 9—9 of FIG. 8.

Although one specific construction of the pusher member 78 has been illustrated in FIGS. 8–10, it is contemplated that the pusher member 78 could have many different constructions. Regardless of the construction of the pusher member 78, the pusher member is used to sequentially push the anchors 24 through the body tissue 22.

Alternative Method of Pushing Anchors

It is contemplated that it may be desired to eliminate the use of the pusher member 78. If this is done, force is transmitted through the series 58 (FIG. 11) of anchors 24 on the thin elongated member 72 to push the leading anchor through the body tissue 22. Thus, the leading anchor 24 is pushed through the body tissue 22 by force transmitted to a trailing end portion 64 of the leading anchor by the next succeeding anchor. After the leading anchor 24 has been pushed through the body tissue by the next succeeding anchor, the next succeeding anchor and the thin elongated member 72 are withdrawn together from the body tissue.

Although the thin elongated member 72 is illustrated in FIG. 11 as being used to guide movement of the anchors 24, the use of the thin elongated member may be dispensed with if desired. The anchors 24 may be guided by only the suture 26. Alternatively, a magazine, similar to the magazine 84 of FIGS. 8 and 9, may be used to guide movement of the anchors 24.

Alternative Method of Closure

In the embodiment of the invention illustrated in FIGS. 1–11, the discontinuity 20 is closed with the inner side surface areas pressing against each other in the manner illustrated in FIGS. 2 and 3. However, it is contemplated that the discontinuity could be closed in a different manner if desired. In the embodiment of the invention illustrated in FIGS. 12 and 13, the body tissue is overlapped with an inner side surface of the body tissue along one side of the discontinuity disposed in engagement with the outer side surface of the body tissue along the opposite side of the discontinuity. Since the embodiment of the invention illustrated in FIGS. 12 and 13 is generally similar to the embodiment of the invention illustrated in FIGS. 1–11, similar numerals will be utilized to designate similar components, the suffix letter "e" being associated with the numerals of FIGS. 12 and 13 to avoid confusion.

A discontinuity 20e in body tissue 22e is closed by anchors 24e. The anchors 24e are interconnected by a suture 26e (FIG. 13). The anchors 24e include an array 30e (FIG. 13) disposed along the outer or upper (as viewed in FIG. 13) side 34e of the discontinuity 20e and an array of anchors 32e disposed along the inner or lower (as viewed in FIG. 13) side 36e of the discontinuity. The anchors 24e in the array 30e of anchors are pressed against an outer side surface 40e of body tissue along the outer side 34e of the discontinuity 20e. The anchors 24e are pressed against the inner side 44e of body tissue 22e along an inner side 36e of the discontinuity 20e.

When the anchors 24e are sequentially positioned relative to the body tissue 22e, the anchors in the outer array 30e of anchors are pushed through the body tissue from the inner side 44e to the outer side 40e. However, the anchors 24e in the inner array 32e of anchors are pushed through the body tissue from the outer side 40e to the inner side 44e of the body tissue. Since the anchors 24e in the inner array 32e of anchors are disposed adjacent to the inner side 44e of the body tissue 22e, it is believed that it will be particularly advantageous to form the anchors 24e and the suture 26e of a material which is capable of being absorbed by body tissue so that the anchors 24e in the inner array 32e of anchors and the suture 26e do not have to be removed. Of course, the anchors 24e in the outer array 30e of anchors may also be formed of a material which is capable of being absorbed by body tissue.

Conclusion

In view of the foregoing description, it is apparent that the present invention provides a new and improved method of closing a discontinuity 20 in body tissue. When a discontinuity 20 in body tissue is to be closed, a suture 26 is inserted through openings 52 in anchors 24 to provide a series 58 of anchors on the suture. In addition, a thin elongated member 72 may be inserted through the openings 52 in the anchors.

The thin elongated member 72 is then inserted through body tissue at a first location disposed along a first side 34 of the discontinuity 20. A first anchor is then pushed through the body tissue 22 with the suture extending through the opening 52 in the first anchor. The thin elongated member 72 is then inserted through body tissue 22 at a second location disposed along a second side 36 of the discontinuity 20. A second anchor 24 is pushed through the body tissue 22 with the suture 26 extending through the opening 52 in the second anchor.

Having described the invention, the following is claimed:

1. A method of closing a discontinuity in body tissue, said method comprising the steps of:

providing a plurality of anchors;

inserting a suture through an opening in each of the anchors to provide a series of anchors on the suture;

forming a first opening in body tissue at a first location which is adjacent to a first side of the discontinuity in the body tissue;

moving a first one of the anchors in the series of anchors through the first opening in the body tissue adjacent to a first side of the discontinuity in the body tissue with the suture extending through the series of anchors;

positioning the first one of the anchors in the series of anchors in engagement with body tissue adjacent to the first side of the discontinuity in the body tissue, said step of positioning the first one of the anchors includes positioning the first one of the anchors in a spaced apart relationship with body tissue adjacent to a second side of the discontinuity in the body tissue and with a first portion of the suture extending through the first opening in the body tissue, a second portion of the suture extending through the first one of the anchors, and a third portion of the suture extending through the first opening in the body tissue along with the first portion of the suture;

forming a second opening in body tissue at a second location which is adjacent to the second side of the discontinuity in the body tissue;

moving a second one of the anchors in the series of anchors through the second opening in the body tissue adjacent to the second side of the discontinuity in the body tissue with the suture extending through the series of anchors;

positioning the second one of the anchors in the series of anchors in engagement with body tissue adjacent to the second side of the discontinuity in the body tissue, said step of positioning the second one of the anchors includes positioning the second one of the anchors in a spaced apart relationship with body tissue adjacent to the first side of the discontinuity in the body tissue and with a fourth portion of the suture extending through the second opening in the body tissue, a fifth portion of the suture extending through the second one of the anchors, and a sixth portion of the suture extending through the second opening in the body tissue along with the fourth portion of the suture;

forming a third opening in body tissue at a third location which is adjacent to the first side of the discontinuity;

moving a third one of the anchors in the series of anchors through the third opening in the body tissue adjacent to the first side of the discontinuity in the body tissue with the suture extending through the series of anchors;

positioning the third one of the anchors in the series of anchors in engagement with body tissue adjacent to the first side of the discontinuity in the body tissue, said step of positioning the third one of the anchors includes positioning the third one of the anchors in a spaced apart relationship with body tissue adjacent to the second side of the discontinuity in the body tissue and with a seventh portion of the suture extending through the third opening in the body tissue, an eighth portion of the suture extending through the third one of the anchors, and a ninth portion of the suture extending through the third opening in the body tissue along with the seventh portion of the suture.

2. A method as set forth in claim 1 wherein said steps of forming a first opening in body tissue and moving a first one of the anchors in the series of anchors through the first opening in the body tissue include pressing a first end of the first one of the anchors against body tissue adjacent to the first side of the discontinuity in the body tissue and pushing the first one of the anchors through the body tissue adjacent to the first side of the discontinuity in the body tissue under the influence of force applied against a second end of the first anchor, said steps of forming a second opening in body tissue and moving a second one of the anchors in the series of anchors through the second opening in the body tissue include pressing a first end of the second one of the anchors against body tissue adjacent to the second side of the discontinuity in the body tissue and pushing the second one of the anchors through the body tissue adjacent to the second side of the discontinuity in the body tissue under the influence of force applied against a second end of the second anchor, said steps of forming a third opening in body tissue and moving a third one of the anchors in the series of anchors through the third opening in the body tissue include pressing a first end of the third one of the anchors against body tissue adjacent to the first side of the discontinuity in the body tissue and pushing the third one of the anchors through the body tissue adjacent to the first side of the discontinuity in the body tissue under the influence of force applied against a second end of the third anchor.

3. A method as set forth in claim 2 further including the steps of inserting a thin elongated member through an opening in the first anchor, said step of forming a first opening in body tissue further includes inserting the thin elongated member through body tissue adjacent to the first side of the discontinuity in the body tissue with the thin elongated member extending through the opening in the first anchor, inserting the thin elongated member through an opening in the second anchor, said step of forming a second opening in body tissue further including inserting the thin elongated member through body tissue adjacent to the second side of the discontinuity in the body tissue with the thin elongated member extending through the opening in the second anchor, and inserting the thin elongated member through an opening in the third anchor, said step of forming a third opening in body tissue further includes inserting the thin elongated member through body tissue adjacent to the first side of the discontinuity in the body tissue with the thin elongated member extending through the opening in the third anchor.

4. A method as set forth in claim 1 wherein said steps of forming a first opening in the body tissue and moving a first one of the anchors in the series of anchors through the first opening in the body tissue include pressing the first anchor against body tissue adjacent to the first side of the discontinuity under the influence of force transmitted through the second anchor to the first anchor, said steps of forming a second opening in the body tissue and moving a second one of the anchors through the second opening in the body tissue include pressing the second anchor against body tissue adjacent to the second side of the discontinuity under the influence of force transmitted through the third anchor to the second anchor, said steps of forming a third opening in the body tissue and moving a third one of the anchors in the series of anchors through the third opening in the body tissue includes pressing the third anchor against body tissue adjacent to the first side of the discontinuity under the influence of force transmitted from a fourth anchor in the series of anchors to the third anchor.

5. A method as set forth in claim 1 further including the step of pulling on the suture to press the body tissue along one of the sides of the discontinuity against the body tissue along the other side of the discontinuity with the first and third openings in the body tissue offset along the discontinuity from the second opening in the body tissue.

6. A method as set forth in claim 1 wherein said step of moving the first one of the anchors through body tissue adjacent to the first side of the discontinuity in the body tissue includes moving the first anchor in a direction away from the body tissue adjacent to the second side of the discontinuity in the body tissue, said step of moving the second one of the anchors through body tissue adjacent to the second side of the discontinuity in the body tissue includes moving the second anchor in a direction away from the body tissue adjacent to the first side of the discontinuity in the body tissue, said step of moving the third one of the anchors through body tissue adjacent to the first side of the discontinuity in the body tissue includes moving the third anchor in a direction away from the body tissue along the second side of the discontinuity in the body tissue.

7. A method as set forth in claim 1 further including pressing the body tissue adjacent to the first side of the discontinuity against the body tissue adjacent to the second side of the discontinuity under the influence of force transmitted between the first, second and third anchors with a portion of the suture which extends from a location adjacent to the first anchor to a location adjacent to the second anchor and a portion of the suture which extends from a location adjacent to the second anchor to a location adjacent to the third anchor disposed between the body tissue adjacent to the first side of the discontinuity and the body tissue adjacent to the second side of the discontinuity.

8. A method as set forth in claim 1 wherein the discontinuity in the body tissue is a longitudinally extending discontinuity, said step of moving a second one of the anchors through the body tissue adjacent to the second side of the discontinuity being performed at a location which is offset longitudinally along the discontinuity from the location where said step of moving a first one of the anchors through the body tissue adjacent to the first side of the discontinuity was performed, said step of moving a third one of the anchors through the body tissue being performed at a location which is offset longitudinally along the discontinuity from the location where said step of moving a second one of the anchors through the body tissue adjacent to the second side of the discontinuity was performed.

9. A method as set forth in claim 1 wherein said step of moving a first one of the anchors through the body tissue includes moving at least a portion of the first anchor through the body tissue adjacent to the first side of the discontinuity with the body tissue in engagement with a portion of the suture which is disposed in engagement with a surface area on the first anchor, said step of moving a second one of the anchors through the body tissue includes moving at least a portion of the second anchor through the body tissue adjacent to the second side of the discontinuity with the body tissue in engagement with a portion of the suture which is disposed in engagement with a surface area on the second anchor, said step of moving a third one of the anchors through the body tissue includes moving at least a portion of the third anchor through the body tissue adjacent to the first side of the discontinuity with the body tissue in engagement with a portion of the suture which is disposed in engagement with a surface area on the third anchor.

10. A method as set forth in claim 1 wherein said step of forming a first opening in body tissue adjacent to a first side of the discontinuity in the body tissue includes inserting a thin elongated member through the body tissue adjacent to the first side of the discontinuity to a position in which an end portion of the thin elongated member extends through the body tissue, said step of moving the first anchor in the series of anchors through the body tissue includes moving the first anchor along the thin elongated member, said step of forming a second opening in body tissue adjacent to a second side of the discontinuity in the body tissue includes inserting the thin elongated member through the body tissue adjacent to the second side of the discontinuity to a position in which the end portion of the thin elongated member extends through the body tissue, said step of moving the second anchor in the series of anchors through the body tissue includes moving the second anchor along the thin elongated member, said step of forming a third opening in body tissue adjacent to the first side of the discontinuity in the body tissue includes inserting the thin elongated member through the body tissue disposed adjacent to the first side of the discontinuity to a position in which the end portion of the thin elongated member extends through the body tissue, said step of moving the third anchor in the series of anchors through the body tissue includes moving the third anchor along the thin elongated member.

11. A method of closing a discontinuity in body tissue, said method comprising the steps of providing a plurality of anchors, inserting a suture and a thin elongated member through an opening in each of the anchors to provide a series of anchors on the suture and the thin elongated member, and positioning each of the anchors relative to the discontinuity in the body tissue, said step of positioning each of the anchors relative to the body tissue includes inserting the thin elongated member into body tissue at a first location which is disposed along a first side of the discontinuity in the body tissue with the series of anchors on the thin elongated member, moving a first one of the anchors in the series of anchors along the thin elongated member into engagement with the body tissue at the first location, removing the thin elongated member from the body tissue at the first location, thereafter, inserting the thin elongated member into body tissue at a second location which is disposed along a second side of the discontinuity in the body tissue with the series of anchors on the thin elongated member, moving a second one of the anchors in the series of anchors along the thin elongate member into engagement with the body of tissue at the second location, said step of moving a second one of the anchors in the series of anchors into engagement with the body tissue at the second location being performed with the suture extending between the first and second anchors, removing the thin elongated member from the body tissue at the second location, thereafter, inserting the thin elongated member into body tissue at a third location which is disposed along the first side of the discontinuity in the body tissue with the series of anchors on the thin elongated member, moving a third one of the anchors in the series of anchors along the thin elongated member into engagement with the body tissue at the third location, said step of moving a third one of the anchors in the series of anchors into engagement with the body tissue at the third location being performed with the suture extending between the first, second and third anchors, and removing the thin elongated member from the body tissue at the third location.

12. A method as set forth in claim 11 wherein said step of moving a first one of the anchors in the series of anchors along the thin elongated member into engagement with the body tissue at the first location includes pushing the first anchor under the influence of force transmitted from the second anchor to the first anchor, said step of moving a second one of the anchors in the series of anchors along the thin elongated member into engagement with the body tissue at the second location includes pushing the second anchor under the influence of force transmitted from the third anchor to the first anchor.

13. A method as set forth in claim 11 wherein said step of moving a first one of the anchors in the series of anchors along the thin elongated member into engagement with the body tissue at the first location includes pushing the first anchor under the influence of force transmitted to the first anchor from a pusher member, said step of moving a second one of the anchors into engagement with the body of tissue at the second location includes pushing the second anchor under the influence of force transmitted to the second anchor from the pusher member, said step of moving a third one of the anchors into engagement with the body tissue at the third location includes pushing the third anchor under the influence of force transmitted to the third anchor from the pusher member.

14. A method as set forth in claim 11 further including the step of moving the first and second sides of the discontinuity in the body tissue toward each other by pulling on the suture.

15. A method as set forth in claim 11 further including the steps of pulling on the suture and moving the suture relative to openings in at least some of the anchors.

16. A method as set forth in claim 11 wherein said step of inserting a suture and a thin elongate member through an opening in each of the anchors includes sequentially inserting the suture and the thin elongated member through an opening in each of the anchors.

17. A method as set forth in claim 14 wherein said step of moving a first one of the anchors into engagement with body tissue at the first location includes moving the first one of the anchors through body tissue which is adjacent to a first side of the discontinuity at the first location, said step of moving a second one of the anchors into engagement with the body tissue at the second location includes moving the second one of the anchors through body tissue which is adjacent to a second side of the discontinuity at the second location, said step of moving a third one of the anchors into engagement with the body tissue at the third location includes moving the third one of the anchors through body tissue which is adjacent to the first side of the discontinuity at the third location.

18. A method of closing a discontinuity in body tissue, said method comprising the steps of providing first and second anchors, inserting a suture and a thin elongated member through an opening in the first anchor, inserting the thin elongated member through body tissue at a first location which is disposed adjacent to a first side of the discontinuity in the body tissue, moving the first anchor along the thin elongated member and through body tissue at the first location with the suture extending through the first anchor, removing the thin elongated member from the body tissue at the first location, inserting the suture and the thin elongated member through an opening in the second anchor, inserting the thin elongated member through body tissue at a second location which is disposed adjacent to a second side of the discontinuity in the body tissue, moving the second anchor along the thin elongated member and through the body tissue at the second location with the suture extending through the first and second anchors, removing the thin elongated member from the body tissue at the second location, and, thereafter, pulling on the suture to urge the body tissue along the first and second sides of the discontinuity toward each other.

19. A method as set forth in claim 18 wherein said step of inserting the suture and the thin elongated member through the opening in the first anchor and said step of inserting the suture and thin elongated member through an opening in the second anchor are performed prior to performance of said step of inserting the thin elongated member through body tissue at the first location.

20. A method as set forth in claim 19 wherein said step of moving the first anchor along the thin elongated member includes pushing the first anchor along the thin elongated member under the influence of force transmitted from the second anchor to the first anchor.

21. A method as set forth in claim 18 wherein said step of moving the first anchor along the thin elongated member and through body tissue at the first location is performed with the suture extending through the second anchor.

22. A method as set forth in claim 18 further including the steps of changing the orientation of the first anchor relative to body tissue at the first location by pulling on the suture after having performed said step of moving the first anchor along the thin elongated member and through body tissue at the first location and changing the orientation of the second anchor relative to body tissue at the second location by pulling on the suture after having performed said step of moving the second anchor along the thin elongated member and through body tissue at the second location.

23. A method as set forth in claim 18 wherein said step of pulling on the suture to urge body tissue along the first and second sides of the discontinuity toward each other includes moving a portion of the suture in the opening in the first anchor relative to the first anchor and moving a portion of the suture in the opening in the second anchor relative to the second anchor.

24. A method as set forth in claim 18 furthering including the steps of providing a third anchor, inserting the suture and the thin elongated member through an opening in the third anchor, inserting the thin elongated member through body tissue at a third location which is disposed along the first side of the discontinuity in the body tissue, moving the third anchor along the thin elongated member and through the body tissue at the third location with the suture extending through the first, second and third anchors, and removing the thin elongated member from the body tissue at the third location.

25. A method as set forth in claim 24 wherein said step of pulling on the suture to urge body tissue along the first and second sides of the discontinuity toward each other includes moving a portion of the suture in the opening in the first anchor relative to the first anchor, moving a portion of the suture in the second anchor relative to the second anchor, and moving a portion of the suture in the third anchor relative to the third anchor.

26. A method as set forth in claim 24 wherein said step of moving the first anchor along the thin elongated member and through body tissue at the first location is performed with the suture extending through the second and third anchors, said step of moving the second anchor along the thin elongated member and through body tissue at the second location being performed with the suture extending through the first and third anchors.

27. A method as set forth in claim 24 wherein said step of inserting the suture and elongated member through the opening in the first anchor, said step of inserting the suture and elongated member through an opening in the second anchor, and said step of inserting the suture through the opening in the third anchor are performed prior to performance of said step of inserting the thin elongated member through body tissue at the first location.

28. A method as set forth in claim 27 wherein said step of moving the first anchor along the thin elongated member includes pushing the first anchor along the thin elongated member under the influence of force transmitted from the third anchor through the second anchor to the first anchor, said step of moving the second anchor along the thin elongated member includes pushing the second anchor along the thin elongated member under the influence of force transmitted from the third anchor to the second anchor.

29. A method as set forth in claim 18 wherein the body tissue has an outer side surface and an inner side surface and the discontinuity in the body tissue extends between the inner and outer side surfaces of the body tissue, said step of moving the first anchor along the thin elongated member and through body tissue at the first location includes moving a leading end portion of the first anchor through the inner side surface of the body tissue at the first location adjacent to the first side of the discontinuity in the body tissue and then through the outer side surface of the body tissue at the first location adjacent to the first side of the discontinuity in the body tissue, said step of moving the second anchor along the thin elongated member and through body tissue at the second location includes moving a leading end portion of the second anchor through the inner side surface of the body tissue at the second location adjacent to the second side of the discontinuity in the body tissue and then through the outer side surface of the body tissue at the second location adjacent to the second side of the discontinuity in the body tissue.

30. A method as set forth in claim 29 wherein said step of pulling on the suture to urge body tissue along the first and second sides of the discontinuity includes pressing the inner side surface of a portion of the body tissue adjacent to the first side of the discontinuity against the inner side surface of a portion of the body tissue adjacent to the second side of the discontinuity.

31. A method comprising the steps of providing first and second anchors, inserting a suture and a thin elongated member through an opening in the first anchor, inserting the suture and the thin elongated member through an opening in the second anchor, inserting the thin elongated member into body tissue at a first location, sliding the first anchor along the thin elongated member into engagement with the body tissue at the first location, said step of sliding the first anchor along the thin elongated member into engagement with body tissue at the first location being performed with the thin elongated member and the suture extending through the openings in the first and second anchors, thereafter, inserting the thin elongated member into body tissue at a second location, and sliding the second anchor along the thin elongated member into engagement with body tissue at the second location, said step of sliding the second anchor along the thin elongated member into engagement with body tissue at the second location being performed with the suture extending through the openings in the first and second anchors.

32. A method as set forth in claim 31 further including transmitting force between the first and second anchors by pulling on the suture with the first anchor in engagement with body tissue at the first location and the second anchor in engagement with body tissue at the second location.

33. A method as set forth in claim 32 wherein said step of sliding the first anchor along the thin elongated member includes pushing the first anchor under the influence of force transmitted from the second anchor to the first anchor.

34. A method as set forth in claim 32 wherein said step of sliding the first anchor along the thin elongated member includes pushing the first anchor under the influence of force transmitted to the first anchor from a pusher member, said step of sliding the second anchor along the thin elongated member includes pushing the second anchor under the influence of force transmitted to the second anchor from a pusher member.

35. A method as set forth in claim 31 further including the step of pulling on the suture and moving a portion of the suture through the opening in the second anchor.

36. A method as set forth in claim 31 wherein said steps of inserting the suture and the thin elongated member through an opening in the first anchor and inserting the suture and the thin elongated member through an opening in the second anchor include inserting the suture through the openings in the first and second anchors and, at a different time, inserting the thin elongated member through the openings in the first and second anchors.

37. A method of closing a discontinuity in body tissue, said method comprising the steps of providing a plurality of anchors, inserting a suture through an opening in each anchor of the plurality of anchors to interconnect the plurality of anchors with the suture, and, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, said step of positioning anchors adjacent to opposite sides of the discontinuity in the body tissue includes inserting a first one of the anchors through body tissue adjacent to a first side of the discontinuity in the body tissue with the suture extending through the opening in the first anchor, thereafter, inserting a second one of the anchors through body tissue adjacent to a second side of the discontinuity in the body tissue with the suture extending through the opening in the second anchor.

38. A method as set forth in claim 37 wherein said step of positioning anchors adjacent to opposite sides of the discontinuity includes inserting a thin elongated member into body tissue adjacent to the first side of the discontinuity in the body tissue, said step of inserting a first one of the anchors through body tissue adjacent to the first side of the discontinuity in the body tissue includes moving the first one of the anchors along the thin elongated member, and inserting the thin elongated member into body tissue adjacent to the second side of the discontinuity in the body tissue, said step of inserting a second one of the anchors through body tissue adjacent to the second side of the discontinuity in the body tissue includes moving the second one of the anchors along the thin elongated member.

39. A method of closing a discontinuity in body tissue, said method comprising the steps of providing a plurality of anchors, inserting a suture through an opening in each anchor of the plurality of anchors to interconnect the plurality of anchors with the suture, and, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, said step of positioning anchors adjacent to opposite sides of the discontinuity in the body tissue includes pushing a first anchor through body tissue disposed along a first side of the discontinuity to move the first anchor from a position in engagement with a first body tissue surface area to a position in engagement with a second body tissue surface area disposed on a side of the body tissue opposite from the first body tissue surface area, pushing a second anchor through body tissue disposed along a second side of the discontinuity to move the second anchor from a position in engagement with a third body tissue surface area to a position in engagement with a fourth body tissue surface area disposed on a side of the body tissue opposite from the third body tissue surface area, and, thereafter, positioning the body tissue along the first side of the discontinuity in engagement with the body tissue along the second side of the discontinuity with the first and third body tissue surface areas facing toward each other.

40. A method of closing a discontinuity in body tissue, said method comprising the steps of providing a plurality of anchors, inserting a suture through an opening in each anchor of the plurality of anchors to interconnect the plurality of anchors with the suture, and, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, said step of positioning anchors adjacent to opposite sides of the discontinuity in the body tissue includes inserting a thin elongated member into body tissue disposed along a first side of the discontinuity in the body tissue with an array of anchors on the thin elongated member and with the suture extending through the openings in the anchors in the array of anchors, moving one of the anchors in the array of anchors along the thin elongated member and through the body tissue along the first side of the discontinuity in the body tissue, thereafter, inserting the thin elongated member into body tissue disposed along a second side of the discontinuity in the body tissue with the array of anchors on the thin elongated member and with the suture extending through the opening in each of the anchors in the array of anchors, moving one of the anchors along the thin elongated member and through the body tissue along the second side of the discontinuity in the body tissue, thereafter, inserting the thin elongated member into body tissue disposed along the first side of the discontinuity in the body tissue with the array of anchors on the thin elongated member and with the suture extending through the opening in each of the anchors and moving one of the anchors along the thin elongated member and through the body tissue along the first side of the discontinuity in the body tissue.

41. A method as set forth in claim 40 wherein said step of positioning anchors adjacent to opposite sides of the discontinuity in the body tissue includes moving each of the anchors through the body tissue with a first end surface of the anchor leading and with the suture extending across the first end surface of the anchor and, thereafter, pulling on the suture to move the first end surface of the anchor toward the body tissue under the influence of force transmitted through the portion of the suture which extends across the first end surface of the anchor.

42. A method of closing a discontinuity in body tissue, said method comprising the steps of providing a plurality of anchors, inserting a suture through an opening in each anchor of the plurality of anchors to interconnect the plurality of anchors with the suture, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, and inserting a thin elongated member through the openings in the plurality of anchors to form an array of anchors on the thin elongated member, said step of positioning anchors adjacent to opposite sides of the discontinuity in the body tissue including inserting the thin elongated member into body tissue along a first side of the discontinuity in the body tissue with the array of anchors on the thin elongated member and with the suture extending through the opening in each of the anchors in the array of anchors, thereafter, moving a first anchor in the array of anchors along the thin elongated member and through the body tissue along the first side of the discontinuity in the body tissue with both the thin elongated member and the suture extending through the opening in the first anchor, thereafter, removing the thin elongated member from the body tissue along the first side of the discontinuity, thereafter, inserting the thin elongated member into body tissue along a second side of the discontinuity in the body tissue with the array of anchors on the thin elongated member and with the suture extending through the opening in each of the anchors in the array of anchors, thereafter, moving a second anchor in the array of anchors along the thin elongated member and through the body tissue along the second side of the discontinuity in the body tissue with both the thin elongated member and the suture extending through the opening in the second anchor, thereafter, removing the thin elongated member from the body tissue along the second side of the discontinuity, thereafter, inserting the thin elongated member into body tissue along the first side of the discontinuity in the body tissue with the array of anchors on the thin elongated member and with the suture extending through the opening in each of the anchors in the array of anchors, thereafter, moving a third anchor in the array of anchors along the thin elongated member and through the body tissue along the first side of the discontinuity in the body tissue with both the thin elongated member and the suture extending through the opening in the third anchor, thereafter, removing the thin elongated member from the body tissue along the first side of the discontinuity.

43. A method of closing a discontinuity in body tissue, said method comprising the steps of providing a plurality of anchors, inserting a suture through an opening in each anchor of the plurality of anchors to interconnect the plurality of anchors with the suture, inserting a thin elongated member through the opening in each anchor of the plurality of anchors, and, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, said step of positioning anchors adjacent to opposite sides of the discontinuity in the body tissue includes inserting the thin elongated member into body tissue and supporting anchors on the thin elongated member with the suture and the thin elongated member extending through the openings in a plurality of the anchors.

44. A method as set forth in claim 43 wherein said step of positioning anchors adjacent to opposite sides of the discontinuity in the body tissue includes moving each of the anchors through the body tissue with a first end surface of the anchor leading and with the suture extending across the first end surface of the anchor and, thereafter, pulling on the suture to move the first end surface of the anchor toward the body tissue under the influence of force transmitted through the portion of the suture which extends across the first end surface of the anchor.

45. A method of closing a discontinuity in body tissue, said method comprising the steps of providing a plurality of anchors, inserting a suture through an opening in each anchor of the plurality of anchors to interconnect the plurality of anchors with the suture, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, and inserting a thin elongated member through the openings in the plurality of anchors to form an array of anchors on the thin elongated member, said step of positioning anchors adjacent to opposite sides of the discontinuity in the body tissue including pushing a first anchor along the thin elongated member and into the body tissue disposed adjacent to a first side of the discontinuity in the body tissue while the suture and the thin elongated member both extend through the openings in the second and third anchors, thereafter, pushing the second anchor along the thin elongated member and into the body tissue disposed adjacent to a second side of the discontinuity in the body tissue while the suture and the thin elongated member both extend through the opening in the third anchor, and, thereafter, pushing the third anchor along the thin elongated member and into the body tissue disposed adjacent to the first side of the discontinuity in the body tissue.

46. A method as set forth in claim 45 wherein said step of inserting a thin elongated member through the openings in the plurality of anchors is performed with the suture extending through the openings.

47. A method as set forth in claim 45 wherein said step of pushing the first anchor along the thin elongated member includes transmitting force from the second anchor to the first anchor.

48. A method as set forth in claim 45 wherein said step of pushing the first anchor along the thin elongated member includes pressing against an end of the first anchor with a presser member.

49. A method of suturing body tissue, said method comprising the steps of providing a plurality of anchors, inserting a suture through an opening in each of the anchors to provide a series of anchors on the suture, pressing a first one of the anchors in the series of anchors against body tissue at a first location under the influence of force transmitted through anchors in the series of anchors to the first anchor and with the suture extending through openings in each of the anchors in the series of anchors, thereafter, pushing the first one of the anchors in the series of anchors into the body tissue at the first location under the influence of force transmitted through the series of anchors to the first anchor and against the influence of force applied against the first anchor by body tissue at the first location and with the suture extending through openings in each of the anchors in the series of anchors, pressing a second one of the anchors in the series of anchors against body tissue at a second location under the influence of force transmitted through anchors in the series of anchors to the second anchor and with the suture extending through openings in each of the anchors in the series of anchors, thereafter, pushing the second one of the anchors in the series of anchors into the body tissue at the second location under the influence of force transmitted through the series of anchors to the second anchor and against the influence of force applied against the second anchor by body tissue at the second location and with the suture extending through openings in each of the anchors in the series of anchors, pressing a third one of the anchors in the series of anchors against body tissue at a third location under the influence of force transmitted through anchors in the series of anchors to the third anchor and with the suture extending through openings in each of the anchors in the series of anchors, and, thereafter, pushing the third one of the anchors in the series of anchors into the body tissue at the third location under the influence of force transmitted through the series of anchors to the third anchor and against the influence of force applied against the third anchor by body tissue at the third location and with the suture extending through openings in each of the anchors in the series of anchors.

50. A method as set forth in claim 49 further including the steps of inserting a thin elongated member through the opening in each of the anchors, inserting the thin elongated member into body tissue at the first location prior to performance of said step of pushing the first one of the anchors in the series of anchors into the body tissue at the first location, said step of pushing the first one of the anchors in the series of anchors into the body tissue at the first location being performed with the thin elongated member extending through the openings in the second and third anchors, inserting the thin elongated member into body tissue at the second location prior to performance of said step of pushing the second one of the anchors in the series of anchors into the body tissue at the second location, said step of pushing the second one of the anchors into the body tissue at the second location being performed with the thin elongated member extending through the opening in the third anchor, and inserting the thin elongated member into body tissue at the third location prior to performance of said step of pushing the third one of the anchors in the series of anchors into body tissue at the third location.

51. A method of suturing body tissue, said method comprising the steps of providing a plurality of anchors, inserting a suture through an opening in each of the anchors to provide a series of anchors on the suture, pressing a leading end of a first one of the anchors in the series of anchors against body tissue at a first location in the body tissue under the influence of force applied against a trailing end of the first one of the anchors in the series of anchors and with the suture extending through openings in each of the anchors in the series of anchors, thereafter, pushing the first one of the anchors in the series of anchors into the body tissue at the first location under the influence of force applied against the trailing end of the first one of the anchors in the series of anchors and against the influence of force applied against the first anchor by body tissue at the first location and with the suture extending through openings in each of the anchors in the series of anchors, pressing a leading end of a second one of the anchors in the series of anchors against body tissue at a second location in the body tissue under the influence of force applied against a trailing end of the second one of the anchors in the series of anchors and with the suture extending through openings in each of the anchors in the series of anchors, thereafter, pushing the second one of the anchors in the series of anchors into the body tissue at the second location under the influence of force applied against the trailing end of the second one of the anchors in the series of anchors and against the influence of force applied against the second anchor by body tissue at the second location and with the suture extending through openings in each of the anchors in the series of anchors, pressing a leading end of a third one of the anchors in the series of anchors against body tissue at a third location in the body tissue under the influence of force applied against a trailing end of the third one of the anchors in the series of anchors and with the suture extending through openings in each of the anchors in the series of anchors, and, thereafter, pushing the third one of the anchors in the series of anchors into the body tissue at the third location under the influence of force applied against the trailing end of the third one of the anchors in the series of anchors and against the influence of force applied against the third anchor by body tissue at the third location and with the suture extending through openings in each of the anchors in the series of anchors.

52. A method as set forth in claim 51 further including the steps of inserting a thin elongated member through the opening in each of the anchors, inserting the thin elongated member into body tissue at the first location prior to performance of said step of pushing the first one of the anchors in the series of anchors into the body tissue at the first location, said step of pushing the first one of the anchors in the series of anchors into the body tissue at the first location being performed with the thin elongated member extending through the openings in the second and third anchors, inserting the thin elongated member into body tissue at the second location prior to performance of said step of pushing the second one of the anchors in the series of anchors into the body tissue at the second location, said step of pushing the second one of the anchors into the body tissue at the second location being performed with the thin elongated member extending through the opening in the third anchor, and inserting the thin elongated member into body tissue at the third location prior to performance of said step of pushing the third one of the anchors in the series of anchors into body tissue at the third location.

53. A method of closing a discontinuity in body tissue, said method comprising the steps of providing a plurality of anchors, inserting a suture through an opening in each of the anchors to provide a series of anchors on the suture, pushing a first one of the anchors in the series of anchors into body tissue at a first location which is disposed adjacent to a first side of the discontinuity in the body tissue with the suture extending through the series of anchors, said step of pushing the first anchor into body tissue at a first location includes pressing an outer surface of the first anchor against the body tissue at the first location and deflecting the body tissue at the first location under the influence of force applied against the body tissue at the first location by the outer surface of the first anchor, pushing a second anchor in the series of anchors into the body tissue at a second location which is disposed adjacent to a second side of the discontinuity with the suture extending through the series of anchors, said step of pushing the second anchor into body tissue at a second location includes pressing an outer surface of the second anchor against the body tissue at the second location and deflecting the body tissue at the second location under the influence of force applied against the body tissue at the second location by the outer surface of the second anchor, and, thereafter, pressing body tissue adjacent to the first side of the discontinuity against body tissue adjacent to the second side of the discontinuity under the influence of force transmitted between the first and second anchors through the suture.

54. A method as set forth in claim 53 further including the steps of pushing a third one of the anchors in the series of anchors into the body tissue at a third location which is disposed adjacent to the first side of the discontinuity with the suture extending through openings in the series of anchors, said step of pushing the third anchor into body tissue at a third location includes pressing an outer surface of the third anchor against the body tissue at the third location and deflecting the body tissue at the third location under the influence of force applied against the body tissue at the third location by the outer surface of the third anchor, said step of pressing the body tissue adjacent to the first side of the discontinuity against the body tissue adjacent to the second side of the discontinuity includes transmitting force between the first, second and third anchors through the suture.

55. A method as set forth in claim 53 further including the steps of inserting a thin elongated member into body tissue at the first location, said step of pushing the first anchor into body tissue at the first location includes pushing the first anchor along the thin elongated member while the thin elongated member extends into the body tissue at the first location and through the opening in the first anchor, inserting the thin elongated member into body tissue at the second location, said step of pushing the second anchor into body tissue at the second location includes pushing the second anchor along the thin elongated member while the thin elongated member extends into the body tissue at the second location and through the opening in the second anchor.

56. A method of closing a discontinuity in body tissue, said method comprising the steps of providing a plurality of anchors, inserting a suture through an opening in each anchor of the plurality of anchors to interconnect the plurality of anchors with the suture, and, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, said step of positioning anchors adjacent to opposite sides of the discontinuity in the body tissue includes pushing a first one of the anchors through body tissue adjacent to a first side of the discontinuity in the body tissue with the suture extending through the opening in the first anchor, said step of pushing a first one of the anchors through body tissue includes pressing an outer surface of the first one of the anchors against the body tissue, thereafter, pushing a second one of the anchors through body tissue adjacent to a second side of the discontinuity in the body tissue with the suture extending through the opening in the second anchor, said step of pushing a second one of the anchors through body tissue includes pressing an outer surface of the second one of the anchors against the body tissue.

57. A method as set forth in claim 56 wherein said step of positioning the body tissue along the first side of the discontinuity in engagement with the body tissue along the second side of the discontinuity includes pulling on the suture and moving the suture through the openings in at least some of the anchors.

58. A method as set forth in claim 56 further including the steps of inserting a thin elongated member through the opening in each anchor of the plurality of anchors, said step of positioning anchors adjacent to opposite sides of the discontinuity includes inserting the thin elongated member into body tissue adjacent to the first side of the discontinuity in the body tissue, said step of pushing a first one of the anchors through body tissue adjacent to the first side of the discontinuity in the body tissue includes moving the first one of the anchors along the thin elongated member, said step of positioning anchors adjacent to opposite sides of the discontinuity includes inserting the thin elongated member into body tissue adjacent to the second side of the discontinuity in the body tissue, said step of pushing a second one of the anchors through body tissue adjacent to the second side of the discontinuity in the body tissue includes moving the second one of the anchors along the thin elongated member.

59. A method of closing a discontinuity in body tissue, said method comprising the steps of providing a plurality of anchors, inserting a suture through an opening in each anchor of the plurality of anchors to interconnect the plurality of anchors with the suture, and, thereafter, positioning anchors adjacent to opposite sides of the discontinuity in the body tissue, said step of positioning anchors adjacent to opposite sides of the discontinuity in the body tissue being performed with the suture extending through an opening in each anchor of the plurality of anchors, said step of positioning anchors adjacent to opposite sides of the discontinuity in the body tissue includes pushing a first anchor through body tissue disposed adjacent to a first side of the discontinuity, said step of pushing a first one of the anchors through body tissue includes pressing an outer surface of the first one of the anchors against the body tissue and deflecting the body tissue under the influence of force applied against the body tissue by the outer surface of the first one of the anchors, pushing a second anchor through body tissue disposed adjacent to a second side of the discontinuity, said step of pushing a second one of the anchors through body tissue includes pressing an outer surface of the second one of the anchors against the body tissue and deflecting the body tissue under the influence of force applied against the body tissue by the outer surface of the second one of the anchors, and, thereafter, positioning the body tissue along the first side of the discontinuity in engagement with the body tissue along the second side of the discontinuity.

60. A method of suturing body tissue, said method comprising the steps of providing a plurality of anchors, inserting a suture and a thin elongated member through an opening in each of the anchors to provide a series of anchors on the suture and the thin elongated member, thereafter, inserting the thin elongated member into body tissue at a first location, engaging the body tissue at the first location with a leading end portion of a first one of the anchors of the series of anchors, applying force against a trailing end portion of the first one of the anchors while the thin elongated member and suture extend through the openings in each of the anchors of the series of anchors, pushing the first one of the anchors into the body tissue at the first location under the influence of force applied against the trailing end portion of the first one of the anchors while the thin elongated member and suture extend through the openings in each of the anchors of the series of anchors, said step of pushing the first one of the anchors into body tissue at the first location includes deflecting body tissue at the first location under the influence of force applied against the body tissue by the leading end portion of the first one of the anchors, inserting the thin elongated member into body tissue at a second location spaced from the first location, engaging body tissue at the second location with a leading end portion of a second one of the anchors while the thin elongated member extends through the opening in the second one of the anchors and while the suture extends through the openings in each of the anchors of the series of anchors, and pushing the second one of the anchors into the body tissue at the second location under the influence of force applied against the trailing end portion of the second one of the anchors while the thin elongated member extends through the opening in the second one of the anchors and while the suture extends through the openings in each of the anchors of the series of anchors, said step of pushing the second one of the anchors into body tissue at the second location includes deflecting body tissue at the second location under the influence of force applied against the body tissue by the leading end portion of the second one of the anchors.

61. A method as set forth in claim 60 further including the steps of inserting the thin elongated member into body tissue at a third location spaced from the first and second locations, engaging body tissue at the third location with a leading end portion of a third one of the anchors while the thin elongated member extends through the opening in the third one of the anchors and while the suture extends through the openings in the series of anchors, and pushing the third one of the anchors into body tissue at the third location under the influence of force applied against the trailing end portion of the third one of the anchors while the thin elongated member extends through the opening in the third one of the anchors and while the suture extends through openings in each of the anchors of the series of anchors.

62. A method as set forth in claim 60 wherein said step of applying force against a trailing end portion of the first one of the anchors while the thin elongated member and suture extend through each of the anchors of the series of anchors includes pushing against the trailing end portion of the first one of the anchors with the leading end portion of the second one of the anchors.

63. A method as set forth in claim 60 wherein said step of applying force against a trailing end portion of a first one of the anchors while the thin elongated member and suture extend through each of the anchors of the series of anchors includes pushing against the trailing end portion of the first one of the anchors with a pusher member which is at least partially disposed between the leading end portion of the second one of the anchors and the trailing end portion of the first one of the anchors.

64. A method as set forth in claim 60 wherein said step of pushing the first one of the anchors into body tissue at the first location under the influence of force applied against the trailing end portion of the first one of the anchors while the thin elongated member and suture extend through the openings in each of the anchors of the series of anchors further includes moving the first one of the anchors through the body tissue from one side of the body tissue to a second side of the body tissue opposite from the one side.

65. A method of suturing body tissue, said method comprising the steps of providing a plurality of anchors, inserting a suture through an opening in each of the anchors to provide a series of anchors on the suture, pressing a leading end portion of a first one of the anchors against body tissue at a first location by applying force against a trailing end portion of the first one of the anchors, penetrating the body tissue at the first location with the first one of the anchors while the suture extends through openings in each of the anchors of the series of anchors, said step of penetrating the body tissue at the first location with the first one of the anchors includes overcoming resistance applied against the leading end portion of the first one of the anchors by the body tissue at the first location by applying force against the trailing end portion of the first one of the anchors, pressing a leading end portion of a second one of the anchors against body tissue at a second location by applying force against a trailing end portion of the second one of the anchors, and penetrating the body tissue at the second location with the second one of the anchors while the suture extends through openings in each of the anchors of the series of anchors, said step of penetrating the body tissue at the second location with the second one of the anchors includes overcoming resistance applied against the leading end portion of the second one of the anchors by the body tissue at the second location by applying force against the trailing end portion of the second one of the anchors.

66. A method as set forth in claim 65 said method further including the steps of inserting a thin elongated member through an opening in each of the anchors, moving the thin elongated member into the body tissue at the first location with the thin elongated member and the suture extending through openings in each of the anchors of the series of anchors, said step of penetrating the body tissue at the first location with the first one of the anchors includes moving the first one of the anchors axially along the thin elongated member.

67. A method as set forth in claim 66 wherein said step of applying force against a trailing end portion of a first one of the anchors includes pushing against the trailing end portion of the first one of the anchors with a pusher member which is at least partially disposed between the trailing end portion of the first one of the anchors and the leading end portion of the second one of the anchors, said step of penetrating the body tissue at the first location with the first one of the anchors by applying force against the trailing end portion of the first one of the anchors includes moving the pusher member axially along the thin elongated member.

68. A method as set forth in claim 66 further including the steps of moving the thin elongated member into body tissue at the second location with the thin elongated member extending through the opening in the second one of the anchors, said step of penetrating the body tissue at the second location with the second one of the anchors includes moving the second one of the anchors axially along the thin elongated member.

69. A method as set forth in claim 65 further including the steps of pressing a leading end portion of a third one of the anchors against body tissue at a third location by applying force against a trailing end portion of the third one of the anchors, and penetrating the body tissue at the third location with the third one of the anchors while the suture extends through openings in each of the anchors of the series of anchors, said step of penetrating the body tissue at the third location with the third one of the anchors includes overcoming resistance applied against the leading end portion of the third one of the anchors by the body tissue at the third location by applying force against the trailing end portion of the third one of the anchors.

70. A method as set forth in claim 69 wherein said step of overcoming resistance applied against the leading end portion of the first one of the anchors by the body tissue at the first location by applying force against the trailing end portion of the first one of the anchors includes pushing against the trailing end portion of the first one of the anchors with a portion of a pusher member which is disposed between the trailing end portion of the first one of the anchors and the leading end portion of the second one of the anchors, said step of overcoming resistance applied against the leading end portion of the second one of the anchors by the body tissue at the second location by applying force against the trailing end portion of the second one of the anchors includes pushing against the trailing end portion of the second one of the anchors with a portion of a pusher member which is disposed between the trailing end portion of the second one of the anchors and a leading end portion of a third one of the anchors, said step of overcoming resistance applied against the leading end portion of the third one of the anchors by the body tissue at the third location by applying force against the trailing end portion of the third one of the anchors includes pushing against the trailing end portion of the third anchor with a portion of a pusher member.

71. A method as set forth in claim 69 wherein said step of overcoming resistance applied against the leading end portion of the first one of the anchors by applying force against the trailing end portion of the first one of the anchors includes pushing against the trailing end portion of the first one of the anchors with the leading end portion of the second one of the anchors, said step of overcoming resistance applied against the leading end portion of the second one of the anchors by applying force against the trailing end portion of the second one of the anchors includes pushing against the trailing end portion of the second one of the anchors with the leading end portion of the third one of the anchors.

* * * * *

UNITED STATES PATENT AND TRADEMARK OFFICE
CERTIFICATE OF CORRECTION

PATENT NO. : 5,464,426
DATED : November 7, 1995
INVENTOR(S) : Peter M. Bonutti

It is certified that error appears in the above-indentified patent and that said Letters Patent is hereby corrected as shown below:

Column 13, line 8, change "14" to --11--.

Signed and Sealed this

Twenty-sixth Day of March, 1996

Attest:

BRUCE LEHMAN

Attesting Officer     Commissioner of Patents and Trademarks